United States Patent
Bogen et al.

(12)

(10) Patent No.: US 6,294,654 B1
(45) Date of Patent: *Sep. 25, 2001

(54) MODIFIED IMMUNOGLOBULIN MOLECULE INCORPORATING AN ANTIGEN IN A NON-CDR LOOP REGION

(75) Inventors: Bjarne Bogen, Bjerkesvingen 8, 1335 Snaroya; Inger Sandlie, Roaveien 16A, N-0752, Oslo; Sigbjørn Fossum, Oslo; Siri Mjaaland, Oslo; Elin Lunde, Oslo; Ingunn B. Rasmussen, Oslo, all of (NO)

(73) Assignees: Inger Sandlie, Oslo; Bjarne Bogen, Snaroya; Sibjorn Fossum, Oslo, all of (NO)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/860,904

(22) PCT Filed: Jan. 19, 1996

(86) PCT No.: PCT/GB96/00116

§ 371 Date: Sep. 29, 1997

§ 102(e) Date: Sep. 29, 1997

(87) PCT Pub. No.: WO96/22377

PCT Pub. Date: Jul. 25, 1996

(30) Foreign Application Priority Data

Jan. 19, 1995 (GB) .................................. 9501079

(51) Int. Cl.[7] .................................................. C07K 16/46
(52) U.S. Cl. .................................. 530/387.3; 530/388.2; 530/403
(58) Field of Search .............................. 530/387.3, 403, 530/388.2

(56) References Cited

U.S. PATENT DOCUMENTS 5,698,679 * 12/1997 Nemazee ........................ 530/387.3

FOREIGN PATENT DOCUMENTS

WO 89/09393 10/1989 (WO) .
WO 94/14847 7/1994 (WO) .
WO 94/14848 7/1994 (WO) .
WO 95/31483 11/1995 (WO) .

OTHER PUBLICATIONS

S. Weiss et al., "B–lymphoma cells process and present their endogenous immunoglobulin to major histocompatibility complex–restricted T cells", *Proceedings Of The National Academy Of Sciences of The USA*, vol. 86, No. 1, pp. 282–286, Jan. 1989.

T. Brumeanu et al., "Efficient Loading Of Identical Viral Peptide Onto Class II Molecules By Antigenzied Immunoglobulin And Influenza Virus", *The Journal OF Experimental Medicine*, vol. 178, pp. 1795–1799, Nov. 1993.

S. Peifang et al., "Enhanced activation of human T cell clones specific for virus–like particles expressing the HIV V3 loop in the presence of HIV V3 loop–specific polyclonal antibodies", *Clinical and Experimental Immunology*, vol. 97, No. 3, pp. 361–366, Sep. 1994.

O. Brekke et al., "Human IgG isotype–specific amino acid residues affecting complement–mediated cell lysis and phagocytosis", *European Journal Of Immunology*, vol. 24, No. 10, pp. 2542–2547, Oct. 1994.

* cited by examiner

Primary Examiner—David Saunders
Assistant Examiner—Mary Beth Tung
(74) Attorney, Agent, or Firm—Akin, Gump, Strauss, Hauer & Feld, L.L.P.

(57) ABSTRACT

A modified immunoglobulin (Ig) molecule incorporates, preferably in one or more non-CDR loops, one or more foreign antigenic peptides such as a ras peptide. The antigen binding site of the immunoglobulin preferably recognises dendritic antigen presenting cells (APCs). The modified Ig can thus be taken up by dendritic APCs and the foreign antigenic peptide presented on MHC II to naive T-helper cells which stimulate cytotoxic T-cells via the production inter alia of IL-2. Modified Igs of the invention can be used to stimulate the immune system which has apparently become tolerant of a mutant protein, e.g., in the case of certain types of cancer, or it could be used for vaccination against viral infections. The modified Ig can be expressed from recombinant host cells from which it is secreted, notwithstanding the presence of the foreign pepide in a loop of the molecule.

8 Claims, 5 Drawing Sheets

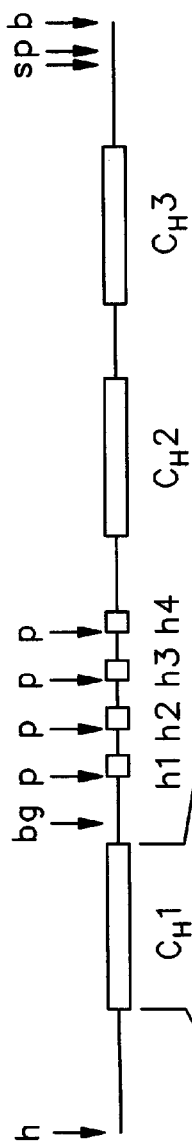

*Fig. 2C* leader
              V-gene
      1 2 3 4 5
G V H S Q V Q L Q (SEQ ID NO:7)     T V S S (SEQ ID NO:8)
5'...ggtgtgcattcccaggtcaattgcag (SEQ ID NO:6) ......acagtctcctcaggtgagttaacgtaccgctagc (SEQ ID NO:9)
       BsmI                                Splice donor HpaI BsiWI HindIII intron
              C-gene
......xxxxxxxxxxxxxx......ggatcc 3'
 Splice acceptor    BamHI

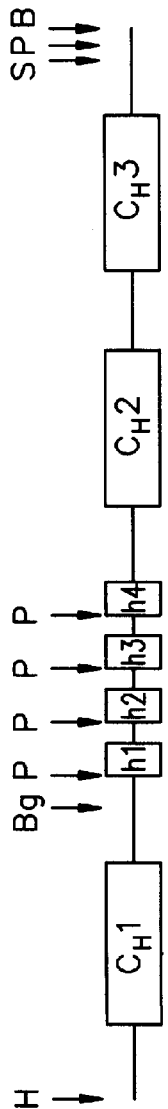

ASTKGPSVFPLAPCSRSTSGGTAALGCLVKDYFPEPVTVSWNSGALTSGVHTFPAV

LQSSGLYSLSSVVTVPSSSLGTQTYTCNVNHKPSNTKVDKRV (SEQ ID NO:1)

1-25 ras  MTEYKLVVVGAGGVGKSALTIQLIQ (SEQ ID NO:10)
5-21 ras      KLVVVGAGGVGKSALTI (SEQ ID NO:11)

Fig. 4C 1-25 ras
5'-acacctgcaacgtgaatcac **atgaccgaatacaaactagtggtggtgggcgcgggcggcgtgggcaagtcagcgctgaccatc
cagctgatccag** accaaggtggacaagagagagt-3' (SEQ ID NO: 12)

5-21 ras
5'-acacctgcaacgtgaatcac aaactagtggtggtgggcgcgggcggcgtgggcaagtcagcgctgaccatc
accaaggtggacaagagagagt-3' (SEQ ID NO: 13)

MODIFIED IMMUNOGLOBULIN MOLECULE INCORPORATING AN ANTIGEN IN A NON-CDR LOOP REGION

FIELD OF THE INVENTION

This invention relates to the activation of T-cells, and particularly for stimulating the body's cell-mediated immune system to deal with infection or cancerous mutations in cells.

BACKGROUND

One of the mechanisms by which the body's immune system operates involves the engulfed of foreign protein by antigen presenting cells (APCs), where the proteins are broken down by proteases into peptide fragments, associated with the cell's MHC II protein in a peptide loading compartment, and then transported to the surface of the APC, where the peptide is presented in association with the MHC II to the T-cell receptors (TCRs) of T-helper cells (CD4+ T-cells). The TCRs of CD4 T-cells only recognise the antigenic peptides in association with MHC II, and the TCRs have a repertoire of recognition sites, so that only those helper cells with the appropriate TCRs will recognise a given antigenic peptide. This activates the helper cell to stimulate cytotoxic T-cells (CD8+ or Tc cells) and B-cells with the corresponding antigen specificity, which then mount an attack on the original source of foreign protein, either directly by CD4+ T-cells themselves, or by the production of antibody (B-cells) or by the Tc-cells. In the case of the latter, receptors on the Tc-cells recognise the original antigen presented in association with MHC I on the surface of cells in which they are endogenously produced, for example as a result of infection or through the generation of a mutated protein within the cell.

Vaccination has been of great importance in the protection against infectious diseases. Even so there is still a need to develop more safe and more effective vaccines. It is also necessary to develop vaccines for diseases for which there until now have been no such preventive measures. For effective vaccination, one needs to activate T-cells of the CD4 type because CD4+ T-cells direct activation of cytotoxic T-cells and B-cells.

Many cancer cells are the result of mutation, for example mutation in the p21 ras gene, and in consequence, an antigenic peptide fragment bearing the mutation is presented at the surface of the cell. The body's immune system may normally deal with such potential cancer cells by receptors on CD4+ T-cells recognising the apparently "foreign" antigen on MHC II and subsequently providing "signal 2" for specific cytotoxic T-cells which may kill the tumour cells. In this way, we probably fight off potential cancers by treating the cancer cells as though they had been infected with a foreign organism. However, in some cases tumours are established, and then it is beneficial to alter the balance between the T-cells and the tumour cells in favour of the T-cells by inducing or increasing specific T-cell activity.

The antigen peptide which locates in the MHC II molecule is typically about 11–20 amino acids in length, and one way of trying to efficiently vaccinate against infectious agents or to activate T-cells specific for tumour specific antigens, is to provide the peptide artificially. However, it has not proved very successful, probably because the peptide is easily degraded.

One group of workers (Zaghouani et al, Science (1993), 259:224–227, and Brumeanu et al, J Exp Med (1993), 178:1795–1799) disclosed the substitution of DNA encoding a viral epitope peptide into the DNA encoding the CDR3 loop of the heavy chain of an immunoglobulin molecule. This gene was co-expressed with a light chain to produce a complete Ig type of molecule, which was taken up by the Fc receptor (FcR) of an APC, and the viral epitope was presented with MHC II on the surface of the APC in vitro. The authors suggested that antigenized self Ig molecules could represent an effective carrier for delivery of peptides to MHC II molecules, as in vaccination or (tolerization) protocols, and a carrier that has a potential to be long-lived and devoid of side-effects.

We have studied antigen presentation of the 91–101 amino acid fragment from the $\lambda 2$ light chain of M315 antibody (Bogen et al, Eur J Immunol (1986), 16:1373). We have further used in vitro mutagenesis to move the epitope to loops in the human IgG3 heavy chain. Three different mutants were made, each with one of the loops of the CH1 domain replaced with the 91–101 peptide. The mutant genes were transfected into a fibroblast cell line which had previously been transfected with genes encoding the $E_\alpha^k E_\beta^d$ MHC II. The resulting clones were assayed for the ability to stimulate $\lambda 2^{315}$ specific T-cell clones. It appears that the mutated heavy chains are retained intracellularly in the transfected fibroblasts, but nevertheless the peptide is processed and presented on MHC II.

SUMMARY OF THE INVENTION

We have found that altered antibodies can be made in which a peptide antigen can be incorporated into a non-CDR loop of an antibody (Ab), and the resulting Ab can be taken up in an APC so that the peptide antigen is presented on the surface of the APC in the context of MHC II, and thereby produce an immune response.

The invention may be used in vaccination against infectious diseases, in which case the peptide antigen, inserted into Ig molecules, should be derived from proteins of the infectious agent. For vaccination purposes, the modified Ig will be targeted to dendritic cells which are especially potent at stimulating naive T-cells.

The invention can also be used in connection with certain types of therapy, the object being to stimulate the immune system which has apparently become tolerant of a particular antigen. For example, many cancers derived from mutations in normal cell proteins may arise because the body's immune system is no longer activated by the mutant protein. Furthermore, the cancer cells are often poor APCs because of a lack of co-stimulatory molecules. A strategy to deal with that, therefore, is to stimulate the body's immune system by presenting it with the mutant protein. Preferably the antigen should be presented on dendritic cells, which are especially potent at stimulating T-cells.

Another aspect of the approach is that peptide antigens presented with MHC II on the surface of APCs stimulate either or both of two types of T-helper cells, Th1 and Th2 respectively. Th1 stimulation results in the production of the cytokines IFN-gamma and IL-2 and the stimulation of cytotoxic T-cells (Tc). Th2 stimulation, on the other hand, results in the production of the cytokines IL-4, IL-5 and IL-10, leading to activation of B-lymphocytes and the production of antibodies to the antigen. Of the two, the Th1 route is preferred for the present approach, since Tc cells are strong antiviral agents. Also, Tc cells (CD8+ T-cells) with specificity for mutant ras peptide have been detected in cancer patients, and such cancer cells should be susceptible to an enhanced Tc immune response.

The preference for the Th1 or Th2 route depends on the dosage and nature of the antigen administered. A stable antigen will have a longer half-life. As Ig molecules seem to be stable inside an APC, its peptides will be produced at a slow rate at the surface of the APC, giving a low steady state concentration of epitope at the surface, but the antigen will be expected to persist in the APC for a long time. Moreover, an Ig molecule is stable in the organism itself, and therefore the APC may be exposed to the antibody for a long time. Thus, the overall effect of our approach should be a long-lasting low level exposure of the immune system to the antigen carried by the Ig, which may be important for eliciting potent T-cell responses.

We have found that immunoglobulin (Ig) molecules, when engulfed by dendritic cells, stimulate specific naive T-cells to IL-2 production. Moreover, we have found that a modified Ig incorporating an antigen peptide can do likewise.

We have demonstrated that a peptide from a CDR loop of an Ig light chain can be transferred to a loop on the heavy chain constant region, and the Ig will still be expressed.

It is crucial that the main outline of the constant domain framework is maintained after introduction of the peptide, since folding, assembly, retention and degradation are tightly coupled events in the endoplasmic reticulum. Since the peptide loop normally facilitates the correct folding together of the adjacent beta-strands, it may be thought of as being important to allow secretion of the correctly folded molecule when transferred to another loop position.

We have, however, also demonstrated that a ras peptide can be placed on a (non-CDR) loop of an Ig and the Ig still be secreted. This is more surprising, since there is stringent "quality control" in the cells which prevent the Ig from being secreted unless it is properly folded, and altering the amino acid sequence of the loop might be thought to cause the protein to fold into a structure which the cell would detect as incorrect, and hence degrade it.

Having thus demonstrated that important foreign peptides can be introduced into non-CDR loops of an Ig, this can be used to stimulate the immune system, and in particular the Tc cell mediated arm, to attack cells expressing proteins containing such a peptide, especially cancer cells and virally infected cells.

To obtain specific fragments on class II molecules we wish to target these peptide fragments to APCS, more particularly to dendritic cells. This can be done by constructing antibody molecules that have variable regions that will bind membrane proteins on dendritic cells, and which in their constant regions have added foreign antigenic peptide fragments. Such modified antibodies will accumulate on the dendritic cells, be endocytosed, and partially degraded. This process will liberate antigenic peptide fragments that can bind to class II molecules. Peptide fragments/class II molecule complexes will then be transported out to the cell membrane for activation ("vaccination") of CD4+ T-cells.

The present invention is therefore concerned with directing an antigenic peptide to the peptide loading compartment of a dendritic cell APC so that it can be efficiently presented at the cell surface with the MHC II molecule. The approach to this is to insert or substitute DNA encoding the antigenic peptide into the gene of an immunoglobulin (Ig) chain at a position corresponding to a loop of an Ig molecule other than its CDR loops, and especially the loops found in the constant region of the Ig molecule.

A polypeptide chain of an Ig molecule folds into a series of parallel beta strands linked by loops. In the variable region, three of the loops constitute the "complementarity determining regions" (CDRs) which determine the epitope binding specificity of the antibody. The loops in the constant region do not have antigen binding specificity, but might have a significant effect on the folding of the Ig molecule and/or its effector or other function.

In our invention, the antigen peptide encoding DNA can be substituted for existing non-CDR loop DNA or can be inserted into it. The resulting altered polypeptide chain can become part of a complete Ig type molecule or a fragment thereof such as Fab by combining it with the other chain of the molecule.

The size of the inserted antigenic peptide is probably not critical, so long as it is sufficient to combine with the MHC II of the APC. Generally an 11 amino acid peptide will suffice, but it could be longer, for example 17 or 20 amino acids.

An antigenic peptide could be inserted into just one non-CDR loop, but it may be desirable to incorporate an antigenic peptide into more than one such loop. This could be the same peptide, so as to increase the amount of antigenic peptide that is carried into the APC; or different antigenic peptides could be incorporated, for example to stimulate a patient's immune system simultaneously with respect to more than one antigen, or to provide on a single molecule antigenic peptides characteristic of more than one strain of an infectious organism or antigenic peptides from the same antigen binding to different MHC II. The loading capacity of the Ig molecule refers to the number of non-CDR loops which may have antigen peptides incorporated into them.

Thus, references to an immunoglobulin or Ig molecule will, unless the context indicates otherwise, be generally construed to include complete Ig-type molecules with intact heavy and light chains, apart from the modifications to incorporate the peptide antigens, fragments of such complete molecules, and single chain versions of the molecule, whether by omitting a heavy or light chain or by covalently linking the chains end-to-end, as well as other variations in the normal Ig molecule as may be desired. The Ig may be of any class or subclass ($IgG_1$, $IgG_2$, $IgG_3$, $IgG_4$, IgA, IgE, IgM etc).

The non-CDR loops utilised may be in the $CH_1$ or $C_K$ region between the hinge region and the variable region. This would apply articularly where the Ig is a Fab fragment. Alternatively or additionally, loops in the Fc region can be used.

A preferred feature of the present invention is that the antigen-binding specificity of the variable region of the Ig molecule is kept unaltered. In this way, the Ig carrying the antigen peptide can be targeted to an appropriate site on the APC by selecting an antibody specific for the relevant surface molecule on the APC. For example, the variable region of the antibody may be specific for an MHC molecule or a marker for dendritic cells, or for an FcR molecule. In the latter case, the modified Ig would bind the FcR by recognition of the variable region, rather than (or possibly in addition to) recognition of the Fc region of the Ig molecule. Entry of the modified Ig into the APC in this way could be regarded as "head first" as distinct from the "sideways" entry in the case of Fc recognition. Sideways entry via FCγI does not necessarily require retention of antigen specificity in the variable region, but there are advantages in having the variable regions with retained antigen specificity, even in that case. A particularly preferred approach is to use antigen binding regions which are for dendritic cell markers. Such a marker is CD11c and antibodies to this marker are also known (N416, ATCC HB224).

Thus, such antibodies, or their variable regions, can be used in the kind of modified antibody constructs described herein. If cross-linking of the antibody on the surface of the dendritic cells is required, this can be provided by employing bispecific antibodies of the present invention, so that one of the variable regions can be specific to a cross-linking entity, or by employing also an antibody against (eg the Fc region of) the altered antibody of the present invention. On the other hand, if the variable region of the Ig is not specific for an APC surface epitope, but rather the Fc region of the altered antibody is used to target the FcR on the APC, the variable region can then be used to bind to a cross-linking entity, the antigen thereby forming an immune complex which is readily taken up via the FcR.

In general, therefore, the advantages of retained antigen-binding specificity for the APC (preferably a dendritic cell) include the following.

- It provides potentially greater binding affinity to APCs than Fc-FcR binding.
- It provides potentially divalent binding, which can increase the likelihood of being taken up by and degraded within the APC.
- It provides the possibility of the Ig molecules being cross-linked by their constant regions, thereby further increasing the likelihood of being taken up by the APC.
- It provides the possibility (in the case of bispecific antibodies) of the Ig molecules being cross-linked by their variable domains, thereby increasing the likelihood of being taken up and correctly processed by the APC, since FcRs are primarily adapted to take up immune complexes.
- It can substantially prevent the Ig from being targeted to the wrong site.
- It allows one in principle to target any of the surface epitopes of the APC, and in particular epitopes specific to dendritic cells.

The present invention therefore provides, inter alia:

- modified Ig molecules having antigenic peptides in one or more non-CDR loops;
- the utilisation of such modified Ig molecules to provide a medicament for immunisation or therapy in a patient, especially where the patient suffers, or is at risk of suffering, from an infection or cellular mutation involving this antigenic peptide.
- DNA encoding such Ig molecules, and the expression of that DNA in a suitable host cell to provide the modified Ig;

BRIEF DESCRIPTION OF THE DRAWINGS

In the accompanying drawings:

FIG. 1 shows:

(A) a restriction map of the human Cγ3 gene. Exons are shown as boxes. h=HindIII, bg=BglII, p=PstI, s=SphI, b=BamHI. PstI and BamHI sites outside the 2.6 kb gene construct reside in the pUC polylinker.

(B) amino acid sequence of the human IgG3 $C_H1$ domain (SEQ ID NO:1). For each mutagenesis reaction one of the segments was replaced with the 91–101 ($\lambda 2^{315}$) epitope (lower line) (SEQ ID NO:2).

(C) nucleotide sequences of the primers used for the in vitro mutagenesis reactions (SEQ ID NO:3–5). The inserted nucleotides encoding the 91–101 epitope are in the central section, with 21 flanking nucleotides on either side.

FIG. 2 shows two expression vectors using the human CMV prorotor to express inserted antibody gene sequences:

(A) pLNOH2 for expression of any heavy V-gene in combination with any C-gene;

(B) pLNOK for expression of any kappa V-gene in combination with a kappa C-gene.

(C) pLNOH2/pLNOK layout (SEQ ID NO:6–9).

Figure 3:
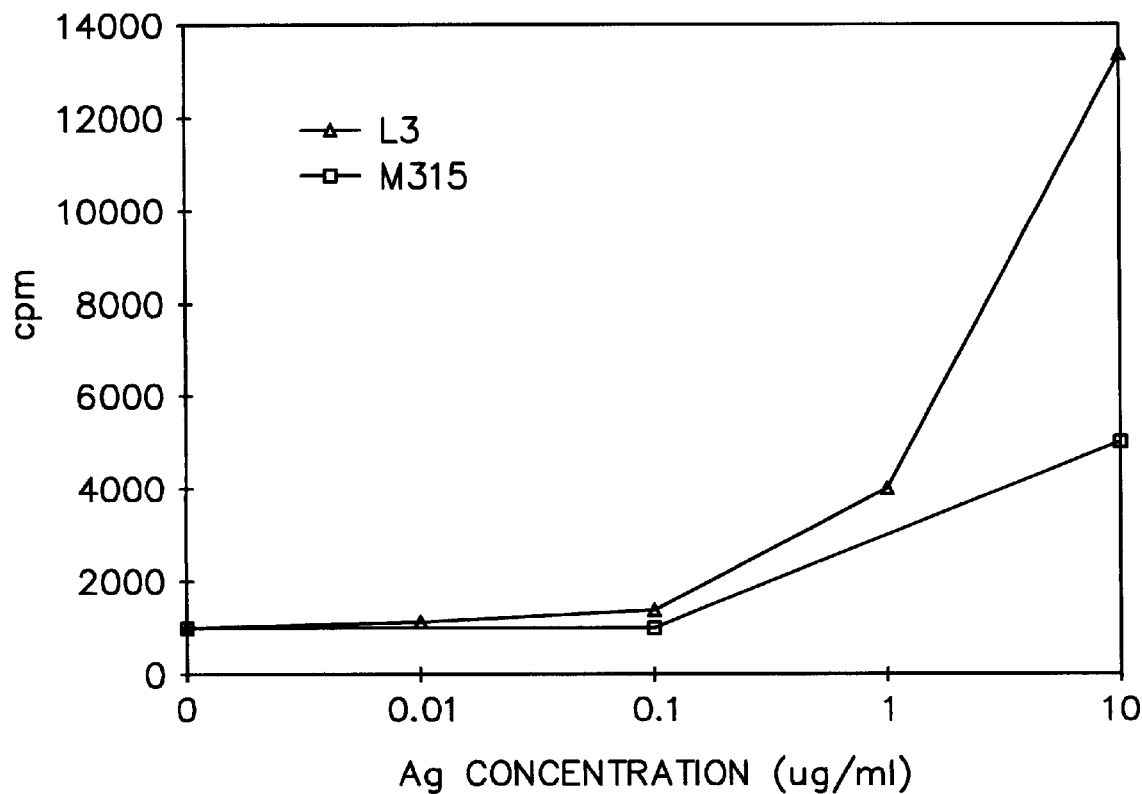

FIG. 3 is a graph showing IL-2 produced after stimulation of lymph node cells with antigenic peptide using the L3 mutant Ab or the native M315 Ab as antigen.

FIG. 4 shows:

(A) The γ3 constant region as cloned in pUC19. Exons are shown as boxes. H=HindIII, Bg=BglII, P=Psti, S=Sphi, B=BamHI. PstI and BamHI sites outside the 2.6 kb gene construct reside in the pUC polylinker.

(B) Amino acid sequence (single letter code) of the human IgG3 $C_H1$ domain (SEQ ID NO:1). The four amino acids constituting the CDR3-corresponding loop in $C_H1$ are shown in bold. These were replaced with amino acids encoding the 1-25 ras or 5-21 ras epitope (SEQ ID NOS:10 & 11, respectively).

(C) Nucleotide sequences of the primers used for the in vitro mutagenesis (SEQ ID NOS:12 & 13). The inserted nucleotides encoding the 1-25 or 5-21 ras epitope are in bold and the 20 nucleotide flanking regions are in non bold.

Figure 5:
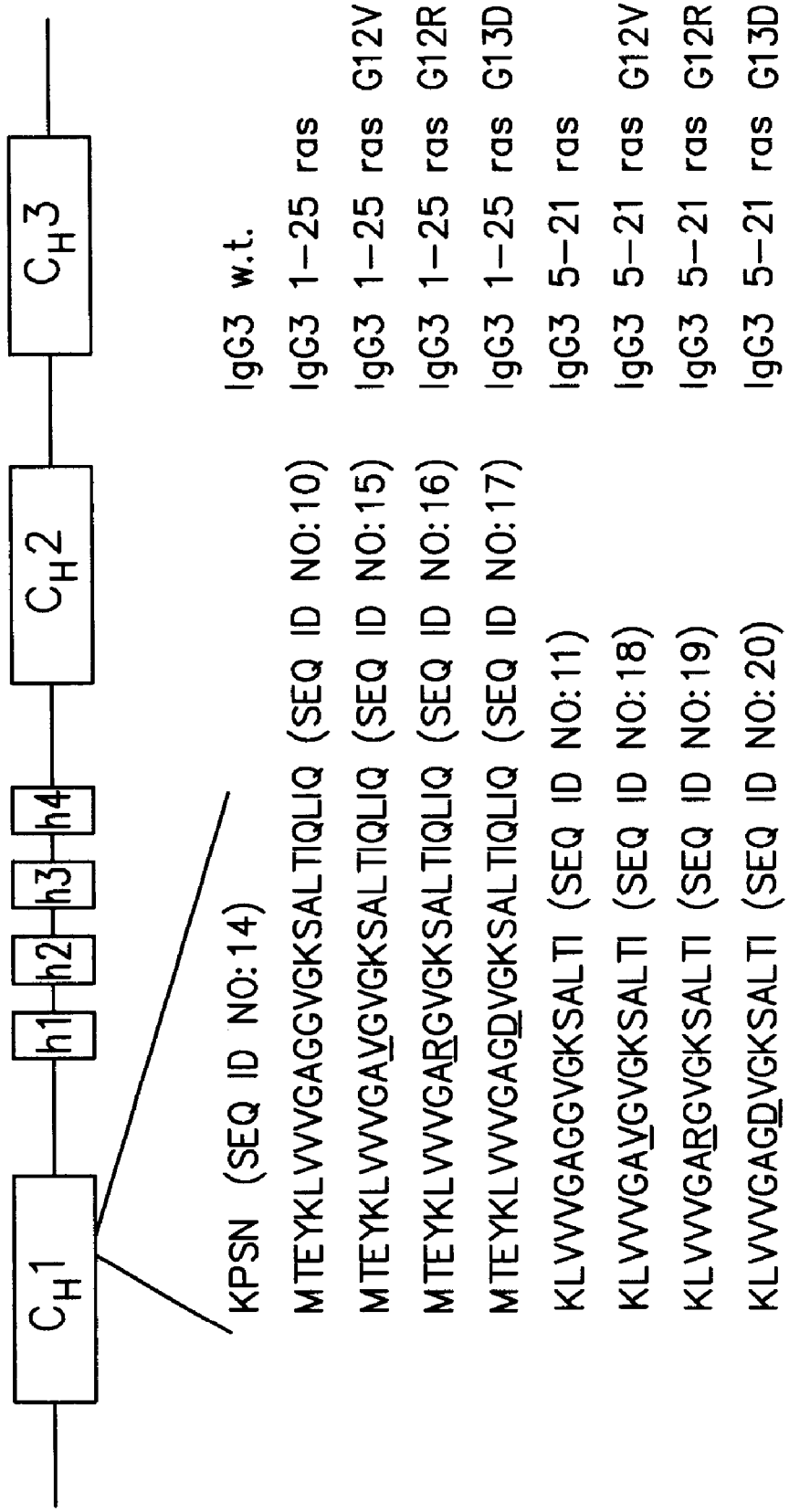

FIG. 5 shows the nomenclature and constructs of constant region genes for IgG3 with different ras epitopes. Exons are shown as boxes. Amino acids constituting the CDR3-corresponding loop are given as single letter aa symbols (SEQ ID NOS:10, 11 & 14–20). Underlined aa are changed relative to the ras w.t. sequence.

DETAILED DESCRIPTION OF THE INVENTION

Production of Modified Igs of the Present Invention

The methods for producing antibodies and antibody fragments by recombinant DNA expression are now well known and utilised. Those methods can be similarly used in carrying out the present invention. Typically, for the production of Fab fragment molecules of the present invention, the V genes are fused with $C_\kappa$(light) and CH1 (heavy) genes in the same vector, and by the same known methods as for production of complete antibodies.

The recombinant DNA methods are further illustrated by the following examples.

The Construction and Expression of Mutant IgG3 Heavy Chains Carrying a CDR3 Loop Peptide Insert FIG. 1 shows the insertion of DNA encoding the 91–101 ($\lambda 2^{315}$) antigenic peptide from the CDR3 region of the M315 Ig myeloma protein at three different positions in the $C_H1$ domain of the human γ3 chain polypeptide. Using conventional in vitro mutagenesis, the inserted DNA encoding the 11 amino acid peptide epitope replaced respectively seven, seven and four amino acids in the L1, L2 and L3 loops of $C_H1$ the new positions of the epitope being chosen such that they were similar for all mutants with respect to secondary structure.

The resulting $C_H1$ encoding fragment is used to replace the wild-type $C_H1$ domain of a complete Cγ3 gene using the HindIII and BglII sites, and the Cγ3 gene can be subcloned as a HindIII-BamHI fragment into an expression vector.

Referring to FIG. 2; these expression vectors are intended for expression of Igs from PCR-amplified V-genes together with a genomic C-gene construct. The vectors have the following features.

Allows expression of intact V-genes. Whole, intact V-genes are amplified using PCR-primers within the leader region and the constant region respectively.

Allows easy subcloning of V-genes. Non-abundant restriction sites flanking the V-genes are introduced in a PCR-reamplification reaction. Computer analysis of V-genes have been done to exclude restriction sites frequently found within the V-gene coding region.

Allows expression of Ig with any C-gene. The vectors have been constructed with CHγ3 and $C_K$ constant region genes, and these genes may be exchanged with other constant gene sequences.

Contains hCMV-promotor. The hCMV-promotor gives high expression in several mammalian cell lines.

Neomycin Selection Marker for Stable Expression

SV40 ori for transient expression. Transient expression gives the possibility for fast analysis of the gene product.

Allows isolation of single stranded vector DNA. fl-origin of replication within the vector gives the possibility for isolation of single stranded DNA for direct sequencing and in vitro mutagenesis of the immunoglobulin genes.

No co-transfection of heavy and light chain vectors. A single cloning step makes the combination vector: pLNOH2K. This is an easy way to avoid cotransfection of the two vectors.

In the vector pLNOH2, upstream from the cloning site the vector contains a hCMV promoter and also the murine $V_H$ gene, $V_{NP}$, thus creating a complete chimeric heavy chain gene. The $V_{NP}$ gene segment codes for a $V_H$ chain characteristic of a λ1 light chain-bearing mouse antibody with specificity for the hapten 4 hydroxy-3 nitrophenacetyl (NP) and the iodinated derivative 5 iodo-4 hydroxy-3 nitrophenacetyl (NIP). The pLNOH2 vector also contains a neomycin selection marker that allows selection of stably transfected cells by virtue of their resistance to G-418.

Fab fragments can be produced employing an expression vector (pLNOH2/Fd) which is a modification of pLNOH2, and is made as follows. PCR primers were constructed which hybridized in the 5' intron and in the very 3' end of the CH1 exon of the human Cγ3 gene. The primers were constructed with restriction enzyme tags such that the sense primer 5'-A<u>CGTACG</u>CTAGCTTTCTGGGGCAGGCCAGGCCT-3'(SEQ ID NO:21)

introduced a BsiWI site (underlined), and the non-sense primer

5'-ATC<u>GGATCC</u>TCAAACTCTCTTGTCCACCTTGGT G-3'(SEQ ID NO:22)

introduced a BamHI site (underlined) as well as a stop codon (bold). The PCR product was inserted in pLNOH2 on BsiWI and BamH1 sites to substitute the Cγ3 gene and make pLNOH2/Fd. In pLONH2/Fd the Ig transcript is polyadenylated by the BGH pA site in the vector.

PCR Amplification and Reamplification of the V-genes

The human or mouse heavy and light(kappa) V-gene are amplified with appropriate primers (Larrick et al, BioTechnology, Vol 7, 1989, 934–938; Bendig et al, BioTechnology, Vol 9, 1991, 88–89) within the leader and the constant region if the complete V-genes are to be preserved.

In order to clone the PCR-amplified V-genes into the vector, the V-genes are sequenced and reamplified with primers which hybridize with the v-gene. The primers should also include tags that incorporate (see FIG. 2):

for the 5' primer: a part of the leader sequence with restriction site BsmI for the 3' primer: splice/donor site and restriction site HpaI or BsiWI.

Cloning of the C-genes

The C genes in the vector are exchanged with C genes carrying the antigenic peptides, which are produced as described in FIG. 1.

The vectors have incorporated a human constant γ3 gene (for pLNOH2) and a human constant kappa gene (for pLNOK) on HindIII/BamHI restriction sites. These H/B fragments include introns with branch point signal and splice acceptor signal as well as a poly-A signal in the 3' end. C-genes cloned into the H/B restriction site should include these signals.

Primers for Reamplification

When constructing reamplification primers for a VH-gene the splice donor site aggtgagt should be included (see above).

When constructing primers for a VK-gene the splice donor site tgagtagaa from human kappa J1 segment can be used.

3' VK primer 22147:

5' *cgtacg*ttctactcacgtttgatctccagct 3'(SEQ ID NO:23)
  BsiWI splice VK

5' VK primer 22146:

5' *ggtgtgcattcc*gacattgagctcacc 3'(SEQ ID NO:24)
  BsmI VK

3' VH primer VHTP3F:

5' *cgtacg*actcacctgaggagacggtgac 3'(SEQ ID NO:25)
  BsiWI splice VH

5' VH primer VHTP3B:

5' *ggtgtgcattcc*gaggtccaactgcag 3'(SEQ ID NO:26)
  BsmI VH

The sequences given in italics are examples of V-sequences. The primers constructed should in each case be complementary to the actual V-genes that are to be amplified.

Combination of the Two Vectors in One

PLNOK is cut with BglII and BamHI. This makes a fragment containing the hCMV promotor, V-gene and the Kappa gene. The fragment can be inserted into the pLNOH2 vector at a BamHI site in either direction.

The above two vectors can be used in non-B cells, such as fibroblast host cells, to express the Ig chains under the hCMV promoter, which gives high level expression. If a plasma host cell is used, these vectors with the hCMV promoter can also be employed, although the natural Ig promoter would function, albeit at a lower level of expression.

Expression of the Mutant Heavy Chain in J558L Cells Using an Ig Promoter

The mutant C3 genes were subcloned as Hind III-BamHI fragments (see FIG. 1) into the vector pSV2gptV$_{NP}$ [Neuberger et al. 1985, Nature 314:268–271]. These constructs were transfected into the J558L cell line. 2×10$^7$ cells and 20 g DNA in 800 1 PBS was transfected using electroporation conditions of 3.5 kV/cm and 25° F. The J558L cell line is a plasmacytoma cell line which is no longer producing its heavy chain. When transfected with heavy chain genes, however, complete Ab can be produced and secreted.

Ab containing L3 mutant heavy chains (see FIG. 1) were isolated from the growth medium of the transfected cells by use of two successive columns coated with Protein A and Protein G, respectively. The Protein A column was used to remove some of the contaminating Ab from the FCS, but will not bind human IgG3. The mutant L3 Ab was eluted from the Protein G column with 0.1 M glycine-HCl, pH 2.7.

Isolation of Spleen Cells Enriched for Dendritic Cells

Spleens were injected with 0.5 ml 100 U/ml collagenase type IV and incubated for 5 min, and then the spleen cells were isolated. The red blood cells were lysed in ACT and the remaining cells incubated in petri dishes at 37° C. for 2 h. Nonadherent cells were removed, fresh medium added and the dishes were incubated over night at 37° C. After swirling of the dishes, nonadherent cells were collected and used for the T cell activation experiments.

T Cell Activation Assays for Exogenously Added Antigenic L3 Ab

Lymph node (LN) cells from T cell receptor transgenic mice [Bogen et al, Eur J Immunol (1992), 22:703–709] were used as T cells, and as APC, BALB/c spleen cells enriched for dendritic cells were employed. LN cells ($10^5$/well) and irradiated (2000 rad) spleen cells ($10^4$/well) were cocultured in triplicates with various amounts of antigenic L3 Ab. Two days later, the cultures were pulsed for 24 h with 1 $\mu$Ci [$^3$H]dThd, and [$^3$H]dThd incorporation counted. Just prior to pulsing of the cells, samples of the supernatant was removed. Their IL-2 content was measured by the use of the IL-2 dependent CTLL cell line, as previously described [Lauritzen, G. F. and Bogen, B. 1991, Scand. J. Immunol. 33, 647–656].

Results from a T Cell Assay with Exogenously Added Antigenic L3 Ab

We wanted to see if the antigenic peptide could be excised from the L3 mutant heavy chain and presented to T cells also when added exogenously to APC. APC (spleen cells) and T cells (LN cells) were cocultured in triplicates in medium containing various amounts of L3 Ab. A positive control using 10 $\mu$g/ml synthetic 91–101($\lambda 2^{315}$) peptide as antigen was also included. T cell proliferation was measured both by incorporation of [$^3$H]dThd, and by IL-2 secretion into the culture supernatant. The results from the IL-2 measurements are given in FIG. 3. The most IL-2 (incorporation of [$^3$H]dThd into CTLL cells, cpm) was measured in the controls using synthetic peptide as antigen (not shown). The average cpm from these controls was 42,276, approximately three times as much as with 10 $\mu$g/ml L3 antigen. With increasing amounts of antigenic M315 or L3 Ab, however, significant levels of IL-2 was secreted into the culture supernatant. Notably, it seems that the peptide is more efficiently presented when located in the L3 mutant than when in its original position in M315. Very similar results were obtained when measuring T cell proliferation.

The Construction of an Altered IgG3 Heavy Chain Carrying Various Mutant ras Peptide Inserts Immunological Reagents The antibodies and conjugates used for ELISA were made in our laboratory. Biotinylation was performed as described [Goding J. W. (1986) Monoclonal Antibodies: Principles and Practice. Sc.ed. Academic Press, London]. Biotin-X-NHS was obtained from Calbiochem Corporation (La Jolla, Calif.). The hapten NIP/NP labeling of BSA or Sepharose has been described [Michaelsen T. E., Aase A., Westby C. and Sandlie I. (1990) Enhancement of complement activation and cytolysis of human IgG3 by deletion of hinge exons. Scand J Immunol 32, 517–528; and Sandlie I., Aase A., Westby C. and Michaelsen T. E. (1989) C1q binding to chimeric monoclonal IgG3 antibodies consisting of mouse variable regions and human constant regions with shortened hinge containing 15–47 amino acids. Eur J Immunol 19, 1599–1603.]. NIP and NP/NIP-Cap-o-Su were purchased from Cambridge Research Biochemicals Ltd., Cambridge, UK.

In Vitro Mutagenesis and Construction of Mutant IgG3 Heavy Chain Genes (1) Construction of Genes Encoding IgG3 1-25ras and IgG3 5-21ras The human $\gamma 3$ constant region gene (coding for the G3m(b°) allotype) is contained on a 2.6 kb HindIII-SphI fragment cloned into the polylinker of pUC19 (a gift from M.-P. Lefranc, Laboratoire d' Immunogénétique, Université des Science, et Techniques du Languedoc, Montpellier, France) (pUC$\gamma$, FIG. 4A). A 0.9 kb HindIII-PstI fragment encoding the $C_H1$ domain was subcloned into the polylinker of M13mp18. In vitro mutageresis was performed as described by Kunkel and others [Kunkel T. A., Roberts J. D. and Zakour R. A. (1987) Rapid and efficient site-specific mutagenesis without phenotypic selection. Meth Enzymol 154, 367–382; and Sanger F., Nicklen S. and Coulson A. R. (1977) DNA sequencing with chain terminating inhibitors. Proc Natl Acad Sci USA 74, 5463–5467.]. To ensure efficient annealing in spite of the large heteroduplex generated, we chose to have flanking regions of 20 nucleotides on each side of the mutagenic core nucleotides. FIGS. 4B and C show the amino acids changed and the primers (SEQ ID NOS:12 & 13) used.

Reagents and E.coli strains used for mutagenesis were purchased from BIO RAD laboratories (Richmond, Calif., USA) and synthetic oligonucleotides from the DNA Synthesis Laboratory, University of Oslo or from MedProbe AS (Oslo, Norway). Screening for mutants was facilitated by the introduction of a unique SpeI restriction site. The mutations were verified by sequencing employing the Sanger dideoxy chain termination method (5). Reagents used were supplied in the SEQUENASE® 2.0 commercial reagent kit from United States Biochemicals (Cleveland, Ohio, USA).

(2) Construction of Genes Encoding IgG3 1-25ras and IgG3 5-21ras with Single Amino Acid Substitutions in the ras Epitope To introduce single amino acid substitutions in the ras epitope in IgG3 1-25 ras and IgG3 5-21 ras, the $C_H1$ domain from these gene constructs was cloned into M13mp18. These constructs served as templates for the in vitro mutagenesis reactions. The mutations introduced were as follows:

The primer 5'-tgggcgcggtgggcgtgggc-3'(SEQ ID NO:27) was used to make the 12Gly→Val mutation (IgG3 1-25rasG12V and IgG3 5-21rasG12V (SEQ ID NOS:15 & 18 respectively)), the primer 5'-gtgggcgcgcggggcgtgggc-3' (SEQ ID NO:28) was used to make the 12Gly→Arg mutation (IgG3 1-25rasG12R and IgG3 5-21rasG12R) (SEQ ID NOS:16 & 19, respectively), and the primer 5'-gcgcgggcgacgtgggcaagt-3'(SEQ ID NO:29) was used to make the 13Gly→Asp mutation (IgG3 1-25rasG13D (SEQ ID NOS:17 & 20, respectively) and IgG3 5-21rasG13D). Nucleotides in bold mark the sites of mutations. FIG. 5 depicts the resulting mutant IgG3 heavy chain genes.

The mutated $C_H1$ fragments were substituted for corresponding wild type (w.t.) sequences on HindIII-BglII sites in pUC$\gamma$. The mutant IgG3 heavy chain genes, as well as the w.t. gene, were cloned as HindIII-BamHI fragments into the vector pLNOH2 (see FIG. 2). Upstream from the cloning site, this vector contains a hCMV promoter and also the murine $V_H$ gene, $V_{NP}$, thus creating a complete chimeric heavy chain gene. The $V_{NP}$ gene segment codes for a $V_H$ chain characteristic of a $\lambda 1$ light chain-bearing mouse antibody with specificity for the hapten 4 hydroxy-3 nitrophenacetyl (NP) and the iodinated derivative 5 iodo-4 hydroxy-3 nitrophenacetyl (NIP). The pLNOH2 vector also contains a neomycin selection marker that allows selection of stably transfected cells by virtue of their resistance to G-418.

Cell Culture and Gene Transfer

The mutant heavy chain genes were introduced into the murine myeloma cell lines J558L (a gift from Dr. S. L. Morrison, Dept. of Microbiology, Molecular Biology Institute, UCLA) or NS0 (obtained from ATCC) by electroporation. J558L produces a λ1 light chain but expresses no heavy chain of its own. The Vλ of the endogenous light chain complements the $V_{NP}$ of the transfected heavy chain to yield an NP-specific antibody. NS0 does not make any immunoglobulin polypeptide at all, and was therefore transfected with a combination vector made of pLNOH2 containing the IgG3 heavy chain genes and the vector pLNOK (see FIG. 2) containing a human κ light chain gene inserted downstream of an irrelevant mouse variable gene. Thus, the antibodies secreted from NS0 do not bind the haptens NP/NIP.

J558L cells were maintained in RPMI 1640 and NS0 in DMEM supplemented with 10% foetal calf serum, 100 U/ml penicillin and 100 μg/ml streptomycin (all from Gibco BRC, Paisley, Scotland) at 37° C. and 5%$CO_2$.

Transfections were carried out by subjecting $2 \times 10^7$ cells and 20 μg plasmid in 0.8 ml ice-cold PBS to an electric field of 3.5 kV/cm using a capacitance setting of 25 μF. Cells were then diluted in regular medium and seeded in 24 well tissue culture dishes. After incubation for 24 hours, transfectants were selected in medium supplemented with 800 μg/ml G-418 (Gibco). Colonies of stably transfected cells were visible after approximately 2 weeks. The transfection efficiency was about $5 \times 10^{-5}$.

Quantification of Chimeric Antibodies

The amount of IgG3 secreted by transfectants was measured by ELISA. Microtitre plates were coated overnight at 4° C. with 1 μg/ml BSA-NIP or 2 μg/ml polyclonal sheep anti-human IgG (Fab specific) in PBS/0.02% azide. After washing several times with PBS containing 0.05% Tween 20 (PBS/T), 100 μl cell supernatant were added to each well and incubated at 37° C. for 1.5 h. After washing as above, a second layer was added, consisting of biotin-labeled polyclonal sheep anti-human IgG (γ chain specific) (1:8000) together with streptavidin and biotin-labeled alkaline phosphatase (1:6000) in PBS/T. After an additional 1.5 h incubation at 37° C. and repeated washing with PBS/T, bound antibody was revealed by addition of the substrate p-nitrophenylphosphate (Sigma). The reaction was carried out for 20–60 min at 37° C. before absorbance at 405 nm was measured on a Dynatech MR 700 Microplate Reader. Standard curves of antibodies were constructed by measuring the absorbance of serial dilutions of affinity purified human IgG that previously had been quantitated by ELISA and by measuring absorbance at 280 nm.

Secretion of Mutant Antibodies from J558L and NS0 Cells

J558L was transfected with the heavy chain gene constructs described in FIG. 5. NS0 was transfected with the IgG3 w.t., IgG3 1-25ras and IgG3 5-21ras heavy chain gene constructs together with the κ light chain gene. The amount of antibodies secreted was determined by an ELISA reaction where the hapten antigen (NIP-BSA) was used as coat. Since normal levels of antibody were detected, this shows that the antigen specificity is retained after introduction of the peptide in CH1.

The amount of antibodies secreted by J558L transfectants is summarized in Table 1.

The amount of antibodies secreted from NS0 transfectants does not differ significantly from the J558L transfectants (see Table 2). However, we have recently obtained individual clones of NS0 transfectants which secrete 5–10 μg/ml of IgG3 1-25ras and IgG3 5-21ras antibodies (data not shown).

TABLE 1

Amount of antibodies secreted by J558L transfectants

| Antibody produced | Secretion level (μg/ml)[1] | Fraction of stably transfected cells secreting antibodies (%)[2] |
|---|---|---|
| IgG3 w.t. | 0.90 ± 0.70 | 95 |
| IgG3 1-25ras | 0.40 ± 0.60 | 50 |
| IgG3 1-25ras G12V | 0.65 ± 0.50 | 61 |
| IgG3 1-25ras G12R | 0.60 ± 0.60 | 57 |
| IgG3 1-25ras G13D | 0.65 ± 0.65 | 83 |
| IgG3 5-21ras | 0.60 ± 0.50 | 70 |
| IgG3 5-21ras G12V | 0.70 ± 0.60 | 58 |
| IgG3 5-21ras G13D | 1.10 ± 1.00 | 48 |

[1]Secretion level for the different transfectants as determined by ELISA (described in Materials and methods). Measurements were made from 20–50 individual colonies of each of the J558L transfectants.
[2]The fraction of individual colonies secreting antibodies as determined by ELISA.

TABLE 2

Amount of antibodies secreted by NS0 transfectants

| Antibody produced | Secretion level (μg/ml)[1] | Fraction of stably transfected cells secreting antibodies (%)[2] |
|---|---|---|
| IgG3 w.t. | 1.50 ± 1.30 | 100 |
| IgG3 1-25ras | 0.90 ± 0.60 | 35 |
| IgG3 5-21ras | 1.40 ± 1.40 | 67 |

[1]Secretion level for the transfectants as determined by ELISA (described in Materials and methods). Measurements were made from 20–40 individual colonies of each of the NS0 transfectants.
[2]The fraction of individual colonies secreting antibodies as determined by ELISA.

What is claimed is:

1. A modified immunoglobulin molecule or functional fragment or part thereof (herein referred to as a modified Ig), having an antigenic peptide foreign to the Ig incorporated in one or more non-CDR loops, and wherein the main outline of the constant domain framework is maintained.

2. A modified Ig of claim 1, wherein an antigen binding domain of the Ig recognises a cell surface molecule of an antigen presenting cell (APC).

3. A modified immunoglobulin or functional fragment or part thereof (herein referred to as a modified Ig), having a foreign antigenic peptide that is foreign to the Ig incorporated in the Ig structure at a position corresponding to a loop of the Ig other than the Ig's CDR loops, and a recognition site for dendritic antigen-presenting cells (herein referred to as dendritic APCs), and wherein the main outline of the constant domain framework is maintained.

4. A modified Ig according to claim 3 wherein the recognition site for dendritic APCs is provided by an antigen binding site of the Ig.

5. A modified Ig according to claim 1 wherein the antigenic peptide is incorporated into one or more loops of a constant region of a heavy or light chain of the Ig.

6. A modified Ig of according to claim 1 wherein the antigenic peptide represents a tumorigenic mutation in a cellular protein.

7. A modified Ig of according to claim 1 the antigenic peptide represents an epitope of a virus or other infective organism.

8. A modified Ig of claim 1 for therapeutic or prophylactic use.

* * * * *

SEQUENCE LISTING

<160> NUMBER OF SEQ ID NOS: 29

<210> SEQ ID NO 1
<211> LENGTH: 98
<212> TYPE: PRT
<213> ORGANISM: Homo sapiens

-continued

<400> SEQUENCE: 1

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val

<210> SEQ ID NO 2
<211> LENGTH: 11
<212> TYPE: PRT
<213> ORGANISM: Homo sapiens

<400> SEQUENCE: 2

Ala Leu Trp Phe Arg Asn His Phe Val Phe Gly
1               5                   10

<210> SEQ ID NO 3
<211> LENGTH: 75
<212> TYPE: DNA
<213> ORGANISM: Artificial Sequence
<220> FEATURE:
<223> OTHER INFORMATION: Description of Artificial Sequence: Primer

<400> SEQUENCE: 3
gcctgagttc cacgacaccg taccgaaaac aaaatggttt ctgaaccata gagccttgac      60
caggcagccc agggc                                                      75

<210> SEQ ID NO 4
<211> LENGTH: 75
<212> TYPE: DNA
<213> ORGANISM: Artificial Sequence
<220> FEATURE:
<223> OTHER INFORMATION: Description of Artificial Sequence: Primer

<400> SEQUENCE: 4
ggacaccacg ctgctgaggg aaccgaaaac aaaatggttt ctgaaccata gagcgacagc      60
cgggaaggtg tgcac                                                      75

<210> SEQ ID NO 5
<211> LENGTH: 75
<212> TYPE: DNA
<213> ORGANISM: Artificial Sequence
<220> FEATURE:
<223> OTHER INFORMATION: Description of Artificial Sequence: Primer

<400> SEQUENCE: 5
aactctcttg tccaccttgg taccgaaaac aaaatggttt ctgaaccata gagcgtgatt      60
cacgttgcag gtgta                                                      75

<210> SEQ ID NO 6
<211> LENGTH: 27
<212> TYPE: DNA

```
<213> ORGANISM: Mus sp.
<220> FEATURE:
<221> NAME/KEY: CDS
<222> LOCATION: (1)..(27)

<400> SEQUENCE: 6 ggt gtg cat tcc cag gtc caa ttg cag                          27
Gly Val His Ser Gln Val Gln Leu Gln
 1               5

<210> SEQ ID NO 7
<211> LENGTH: 9
<212> TYPE: PRT
<213> ORGANISM: Mus sp.

<400> SEQUENCE: 7

Gly Val His Ser Gln Val Gln Leu Gln
 1               5

<210> SEQ ID NO 8
<211> LENGTH: 33
<212> TYPE: DNA
<213> ORGANISM: Mus sp.
<220> FEATURE:
<221> NAME/KEY: CDS
<222> LOCATION: (1)..(12)

<400> SEQUENCE: 8 aca gtc tcc tca ggtgagttaa cgtacgctag c                      33
Thr Val Ser Ser
 1

<210> SEQ ID NO 9
<211> LENGTH: 4
<212> TYPE: PRT
<213> ORGANISM: Mus sp.

<400> SEQUENCE: 9

Thr Val Ser Ser
 1

<210> SEQ ID NO 10
<211> LENGTH: 25
<212> TYPE: PRT
<213> ORGANISM: Artificial Sequence
<220> FEATURE:
<223> OTHER INFORMATION: Description of Artificial Sequence: Mutant ras
      sequence

<400> SEQUENCE: 10

Met Thr Glu Tyr Lys Leu Val Val Val Gly Ala Gly Gly Val Gly Lys
 1               5                  10                  15

Ser Ala Leu Thr Ile Gln Leu Ile Gln
            20                  25

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Mutant ras
      sequence

<400> SEQUENCE: 11

Lys Leu Val Val Val Gly Ala Gly Gly Val Gly Lys Ser Ala Leu Thr
 1               5                  10                  15
Ile
```

<210> SEQ ID NO 12
<211> LENGTH: 115
<212> TYPE: DNA
<213> ORGANISM: Artificial Sequence
<220> FEATURE:
<223> OTHER INFORMATION: Description of Artificial Sequence: Primer and synthetic sequence

<400> SEQUENCE: 12
acacctgcaa ctggaatcac atgaccgaat acaaactagt ggtggtgggc gcgggcggcg      60
tgggcaagtc agcgctgacc atccagctga tccagaccaa ggtggacaag agagt          115

<210> SEQ ID NO 13
<211> LENGTH: 91
<212> TYPE: DNA
<213> ORGANISM: Artificial Sequence
<220> FEATURE:
<223> OTHER INFORMATION: Description of Artificial Sequence: Primer and synthetic sequence

<400> SEQUENCE: 13
gcctgagttc cacgacaccg aaactatggg tggtgggcgc gggcggcgtg ggcaagtcag      60
cgctgaccat caccaaggtg gacaagagag t                                    91

<210> SEQ ID NO 14
<211> LENGTH: 4
<212> TYPE: PRT
<213> ORGANISM: Homo sapiens

<400> SEQUENCE: 14

Lys Pro Ser Asn
 1

<210> SEQ ID NO 15
<211> LENGTH: 25
<212> TYPE: PRT
<213> ORGANISM: Artificial Sequence
<220> FEATURE:
<223> OTHER INFORMATION: Description of Artificial Sequence: Mutant ras sequences

<400> SEQUENCE: 15

Met Thr Glu Tyr Lys Leu Val Val Val Gly Ala Val Gly Val Gly Lys
 1               5                  10                  15

Ser Ala Leu Thr Ile Gln Leu Ile Gln
            20                  25

<210> SEQ ID NO 16
<211> LENGTH: 25
<212> TYPE: PRT
<213> ORGANISM: Artificial Sequence
<220> FEATURE:
<223> OTHER INFORMATION: Description of Artificial Sequence: Mutant ras sequences

<400> SEQUENCE: 16

Met Thr Glu Tyr Lys Leu Val Val Val Gly Ala Arg Gly Val Gly Lys
 1               5                  10                  15

Ser Ala Leu Thr Ile Gln Leu Ile Gln
            20                  25

<210> SEQ ID NO 17
<211> LENGTH: 25

```
<212> TYPE: PRT
<213> ORGANISM: Artificial Sequence
<220> FEATURE:
<223> OTHER INFORMATION: Description of Artificial Sequence: Mutant ras
      sequences

<400> SEQUENCE: 17

Met Thr Glu Tyr Lys Leu Val Val Val Gly Ala Gly Asp Val Gly Lys
 1               5                  10                  15

Ser Ala Leu Thr Ile Gln Leu Ile Gln
            20                  25

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Mutant ras
      sequences

<400> SEQUENCE: 18

Lys Leu Val Val Val Gly Ala Val Gly Val Gly Lys Ser Ala Leu Thr
 1               5                  10                  15

Ile

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Mutant ras
      sequences

<400> SEQUENCE: 19

Lys Leu Val Val Val Gly Ala Arg Gly Val Gly Lys Ser Ala Leu Thr
 1               5                  10                  15

Ile

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Mutant ras
      sequences

<400> SEQUENCE: 20

Lys Leu Val Val Val Gly Ala Gly Asp Val Gly Lys Ser Ala Leu Thr
 1               5                  10                  15

Ile

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 21
acgtacgcta gctttctggg gcaggccagg cct                              33

<210> SEQ ID NO 22
<211> LENGTH: 34
<212> TYPE: DNA
<213> ORGANISM: Artificial Sequence
```

```
<220> FEATURE:
<223> OTHER INFORMATION: Description of Artificial Sequence: Primer

<400> SEQUENCE: 22
atcggatcct caaactctct tgtccacctt ggtg                                    34

<210> SEQ ID NO 23
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 23
cgtacgttct actcacgttt gatctccagc t                                       31

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 24
ggtgtgcatt ccgacattga gctcacc                                            27

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 25
cgtacgactc acctgaggag acggtgac                                           28

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 26
ggtgtgcatt ccgaggtcca actgcag                                            27

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 27
tgggcgcggt gggcgtgggc                                                    20

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 28
gtgggcgcgc ggggcgtggg c                                                  21
```

-continued

```
<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 29
gcgcgggcga cgtgggcaag t                                              21
```